United States Patent [19]

Stier et al.

[11] Patent Number: 4,568,534
[45] Date of Patent: Feb. 4, 1986

[54] DENTIFRICES

[75] Inventors: Roger E. Stier, Clifton; James D. Vidra, Lebanon, both of N.J.; Bernard Misek, Pomona, N.Y.

[73] Assignee: Beecham Inc., Clifton, N.J.

[21] Appl. No.: 699,168

[22] Filed: Feb. 7, 1985

Related U.S. Application Data

[63] Continuation-in-part of Ser. No. 613,330, May 23, 1984, which is a continuation-in-part of Ser. No. 571,571, Jan. 17, 1984, abandoned.

[51] Int. Cl.[4] ........................... A61K 7/16; A61K 7/18
[52] U.S. Cl. ....................................... 424/7.1; 424/49; 424/52
[58] Field of Search ............................ 424/7.1, 49–58

[56] References Cited

U.S. PATENT DOCUMENTS 4,016,089  4/1977  Regan et al. ................... 252/106
4,223,003  9/1980  Scheller ........................... 424/7
4,301,141 11/1981  Scheller ........................... 424/7

*Primary Examiner*—Shep K. Rose
*Attorney, Agent, or Firm*—Jacobs & Jacobs

[57] ABSTRACT

A dentifrice containing an anticaries agent and an abrasive is produced to which has been added at least one color indicator which, when the user brushes his or her teeth with the dentifrice, results in a color change in the dentifrice within the user's mouth after a predetermined period of brushing time has elapsed for the purpose of indicating to the user that he or she has brushed his or her teeth a sufficient length of time.

10 Claims, No Drawings ns has brushed sufficiently long.

DENTIFRICES

This is a continuation-in-part of our application Ser. No. 613,330 filed May 23, 1984, which is a continuation-in-part of our application Ser. No. 571,571 filed Jan. 17, 1984, now abandoned.

The present invention relates to dentifrices, and more particularly to improved dentifrices, wherein the improvement comprises incorporating into the dentifrice a buffering system which maintains an alkaline pH for a predetermined period of brushing time and at least one color indicator. When the user brushes his teeth with the dentifrice, the color indicator causes the dentifrice to show a color within the user's mouth either after a predetermined period of time has elapsed or alternatively to show one color upon initial brushing followed by a color change after a predetermined period of time has elapsed. The purpose of the at least one color indicator is to indicate to the user that he or she has brushed his or her teeth a sufficient length of time.

The dentifrice to which the present invention is added can be any of several known in the art which contain, for example, an anticaries agent and an abrasive and can be in paste, gel or other suitable form. By varying the concentration of the buffering system, an alkaline pH is maintained for a predetermined period of brushing time during which the user is brushing his or her teeth with the dentifrice. At the end of the predetermined period of time, the dentifrice will show a different color that it showed at the beginning of the brushing operation.

Dentifrices containing color indicators are known in the art. U.S. Pat. No. 4,301,141 describes the use of gelatin, a gelatinous eggwhite product or a mixture thereof together with at least one surfactant in a high foaming toothpaste where the foam contains a coloring agent which changes during the brushing period. U.S. Pat. No. 4,223,003 describes a dentifrice in paste or powder form which contains a natural or synthetic dye and at least one high foam surfactant so that a color change occurs in the foam during the course of brushing. This patent requires at least 2.5 weight percent of a high foam surfactant.

U.S. Pat No. 4,150,106 describes a toothpaste which changes color during a nonspecific brushing period and which contains as the essential ingredient a citrate/citric acid buffer system and chlorophenol red.

U.S. Pat No 4,016,089 describes a denture cleaning concentrate. U.S. Pat. No. 1,717,723 describes the use of a combination of phenolphthalein and Congo red as a color indicating a means for detecting acidity in the mouth. U.S. Pat. No. 1,112,180 describes the use of phenolphthalein as a coloring indicator in dentifrices to determine whether the mouth is in an acid or alkaline condition.

The present invention differs from the above patents in several respects. First, the dentifrice does not contain at least 2.5 weight percent of a high foam surfactant. Secondly, the buffering system is unique, as the combination of the buffering system, which maintains the dentifrice system at an alkaline pH in a user's mouth for a predetermined period of time during brushing by the user, and the incorporation into the dentifrice of at least one color indicator, which will change the color of the dentifrice after said predetermined period of brushing time as a result of the lowering of the pH by the saliva in the mouth of the user further has not been previously suggested. Thirdly, the length of time over which the pH is lowered may be varied to produce the desired color change at a predetermined period of brushing time by varying the concentration of the buffering system in the dentifrice.

According to a further embodiment of the present invention, two color indicators are used in combination so that when the user begins brushing, the first color indicator gives the dentifrice one color and at the completion of the predetermined period of time for brushing, the second color indicator gives the dentifrice a different color in place of the first color to show the user that he or she has brushed long enough. The second color indicator is one activated by the lowering of the pH by the saliva of the user.

According to one embodiment of the present invention, a suitable pH responsive color indicator such as a dye, for example phenolphthalein, is used which will show one color at the beginning of the brushing period and after a predetermined peiod of brushing time will change color. The color change occurs when the pH of the dentifrice is lowered from its initial alkaline pH to the pH of saliva. At that point in time it shows a different color to indicate to the user that he or she has brushed a sufficient length of time.

According to a further embodiment of the present invention, a combination of pH responsive dyes such as phenolphthalein and FD&C Blue #1, D&C Yellow #10 and the like are used in which the dye combination responds to a lowering of the alkaline pH by the saliva. When the brusher begins to use the dentifrice, the phenolphthalein color will show. After a predetermined period of brushing, the secondary color will appear as the pH is lowered by the saliva in the mouth of the user, thereby replacing the phenolphthalein color.

The dentifrices according to the present invention preferably contain 10–50% humectant, 10–40% deionized water, 20–40% abrasive such as calcium carbonate, dicalcium phosphate, silica, 0.5–2.0% binders, 0.1–0.3% sweetners, $0.5 \propto 5.0\%$ flavorants, 0.005–0.025% colorants, 0.5–2.0% surfactants, 0.20–0.60% sodium hydroxide having an ionic strength and a pH value adapted to yield a final pH for the dentifrice within the range of 10.5–11.5 and 0.70–4.3% of a buffer which is preferably a sodium phosphate di-basic anhydrous-sodium hydroxide combination. In addition, the dentifrice of the present invention contains an effective amount of and anticaries agent such as sodium monofluorophosphate, sodium fluoride or stannous fluoride or the like, alone or in combination. The dentifrice may also contain a desensitizing agent and/or an antimicrobial agent. When phenolphthalein is used as the color indicator, the color of the dentifrice will change from deep pink to white after 30–60 seconds of brushing. When secondary dyes such as D&C Yellow #10 or FD&C Blue #1 are also incorporated, the pink color will disappear and a yellow or blue color will appear after 30–60 seconds of brushing.

According to a further embodiment of the present invention, the dentifrice may be in the form of a striped toothpaste. In that case, the core may be white and have a pH of about 11. The colored stripes, for example blue, are either clear or opaque and contain a suitable pH sensitive dye. The stripes have a pH of about 7. In that embodiment, the toothpaste initially shows as white in the user's mouth. Upon brushing, the dentifrice turns a color, for example pink, and after about 30–45 seconds turns white again to indicate to the user that he or she has brushed a sufficient length of time. Alternatively, the white core may have a pH of about 11 and a colored stripe such as a red stripe having a pH of about 11 may be combined with the white core. On brushing, the dentifrice turns pink and after about 30-45 seconds returns to the white color as the saliva lowers the pH, as was the case with the white core and blue stripes. When the color indicator is incorporated into the stripes of a striped gel toothpaste, this may conveniently be done using a dual compartmentalized tube. The color indicator may also be combined with a second coloring agent if it is desired to have the dentifrice turn a second color other than white at the completion of the predetermined brushing period.

The surfactant used according to the present invention is not a high foaming surfactant. It is preferably an alkali metal salt of a fatty alcohol sulphate, alkane sulphonate and/or amine oxide. A preferred surfactant is the sodium salt of lauryl alcohol sulphate which is a well-known surfactant for this type product. The concentration of surfactant is preferably 1.15%.

The following non-limitative examples more particularly illustrate the present invention:

EXAMPLE 1

A dentifrice according to the present invention was prepared by combining the ingredients set forth below according to known conventional techniques:

| Ingredients | % w/w |
| --- | --- |
| Glycerine | 30.350 |
| Sodium carboxymethylcellulose | 1.350 |
| Veegum F TM | 1.000 |
| Deionized water | 24.890 |
| Sodium monofluorophosphate | 0.760 |
| Sodium saccharin | 0.250 |
| Phenolphthalein solution | 1.000 |
| Sodium hydroxide solution | 0.250 |
| Calcium carbonate | 38.000 |
| Flavorants | 1.000 |
| Sodium lauryl sulfate | 1.150 |
| TOTAL | 100.000 |

EXAMPLE 2

A dentifrice according to the present invention was prepared by combining the ingredients set forth below according to known conventional techniques:

| Ingredients | % w/w |
| --- | --- |
| Glycerine | 30.350 |
| Sodium carboxymethylcellulose | 1.350 |
| Veegum F TM | 1.000 |
| Deionized water | 24.890 |
| Sodium monofluorophosphate | 0.760 |
| Sodium saccharin | 0.250 |
| D&C Yellow #10 dye | 0.005 |
| Phenolphthalein solution | 1.000 |
| Sodium hydroxide solution | 0.250 |
| TOTAL | 100.000 |

EXAMPLE 3

A striped dentifrice according to the present invention was prepared by combining the ingredients set forth below according to known conventional techniques:

| Ingredients | % w/w |
| --- | --- |
| Glycerine | 25.830 |
| Sodium carboxymethylcellulose | 1.350 |
| Veegum F TM | 1.000 |
| Deionized water | 24.890 |
| Sodium monofluorophosphate | 0.760 |
| Sodium saccharin | 0.250 |
| Phenolphthalein solution | 1.000 |
| Sodium hydroxide solution | 0.510 |
| Calcium carbonate | 38.000 |
| Flavorants | 1.000 |
| Sodium lauryl sulfate | 1.150 |
| Dibasic sodium phosphate (anhydrous) | 4.260 |
| TOTAL | 100.000 | and adding thereto a striping material prepared by combining the ingredients set forth below according to known conventional techniques:

| Ingredients | % w/w |
| --- | --- |
| Polyethylene glycol 400 | 3.000 |
| Sodium carboxymethyl cellulose | 0.900 |
| Calcium carrageenan | 0.250 |
| Deionized water | 16.840 |
| Sodium monofluorophosphate | 0.760 |
| Sorbitol 70% | 62.000 |
| Sodium benzoate | 0.200 |
| Sodium saccharin | 0.200 |
| Sodium silicate solution | 0.200 |
| Silica | 13.500 |
| Titanium dioxide | 1.000 |
| Sodium lauryl sulfate | 1.150 |
| TOTAL | 100.000 |

The preparation of dentifrices including striped dentifrices is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices according to the present invention.

What is claimed is:

1. In an alkaline dentifrice containing 0.20-0.6% sodium hydroxide having an ionic strength and a pH value adapted to yield a final pH for the dentifrice within the range of 10.5-11.5 an anticaries fluoride agent and abrasive, the improvement which comprises incorporating into said dentifrice 0.70 to 4.3% of a buffering system which maintains an alkaline pH for a predetermined period of brushing time during which the user is brushing his teeth with the dentifrice, and at least one color indicator showing color at an alkaline pH and which upon contact with saliva causes a color change in the dentifrice within the user's mouth after a predetermined period of time has elapsed for the purpose of indicating to the user that he or she has brushed his or her teeth a sufficient length of time.

2. The improvement according to claim 1 wherein at least one color indicator is a material showing one color at alkaline pH and a different color after said predetermined period of brushing time has elapsed resulting from the lowering of pH by the saliva of the user.

3. The improvement according to claim 1 wherein two color indicators are incorporated in the dentifrice, the first color indicator showing its color at an alkaline pH and the second color indicator showing its color after said predetermined period of brushing time has elapsed resulting from lowering of the pH by the saliva of the user.

4. The improvement according to claim 1 wherein the buffering system is sodium phosphate dibasic-sodium hydroxide combination in an amount sufficient to maintain an alkaline pH for 30–60 seconds of brushing time.

5. The improvement according to claim 1 wherein at least one color indicator is phenolphthalein.

6. The improvement according to claim 3 wherein the two color indicators are phenolphthalein and D&C Yellow #10.

7. The improvement according to claim 1 wherein the anticaries agent in the dentifrice is sodium monofluorophosphate, sodium fluoride, stannous fluoride or a combination thereof.

8. The improvement according to claim 1 wherein the abrasive contained in the dentifrice is calcium carbonate, dicalcium phosphate or silica.

9. The improvement according to claim 1 wherein the dentifrice is in the form of a striped toothpaste havng a central white core and pastel or colored stripes that are either clear or opaque, said core having a pH of about 11 and said stripes containing a pH sensitive dye and having a pH of about 7.

10. The improvement according to claim 1 wherein the dentifrice is in the form of a striped toothpaste having a white central core and pastel or colored stripes that are either clear or opaque, said white core having a pH of about 11 and said stripes containing at least one color indicator and having a pH of about 11.

* * * * *